(12) United States Patent
Passuello

(10) Patent No.: US 8,613,516 B2
(45) Date of Patent: Dec. 24, 2013

(54) OPHTHALMIC ILLUMINATION DEVICE

(76) Inventor: Gianfranco Passuello, Rovereto (IT)

( * ) Notice: Subject to any disclaimer, the term of this patent is extended or adjusted under 35 U.S.C. 154(b) by 0 days.

(21) Appl. No.: 13/699,609

(22) PCT Filed: May 27, 2011

(86) PCT No.: PCT/IB2011/052330
§ 371 (c)(1),
(2), (4) Date: Dec. 11, 2012

(87) PCT Pub. No.: WO2011/148349
PCT Pub. Date: Dec. 1, 2011

(65) Prior Publication Data
US 2013/0077051 A1    Mar. 28, 2013

(30) Foreign Application Priority Data
May 27, 2010    (IT) .............................. TN20100008 U

(51) Int. Cl.
*A61B 3/10*    (2006.01)
(52) U.S. Cl.
USPC .......................................... 351/221; 351/246
(58) Field of Classification Search
USPC .................... 351/205, 219, 221, 246
See application file for complete search history.

(56) References Cited

U.S. PATENT DOCUMENTS 3,602,581 A * 8/1971 Heine ........................... 351/211

FOREIGN PATENT DOCUMENTS

| DE | 4101794 | 7/1992 |
|---|---|---|
| EP | 1844702 | 10/2007 |
| EP | 1964511 | 9/2008 |
| GB | 2123977 | 2/1984 |
| JP | 8098811 | 4/1996 |
| WO | 2011/045190 | 4/2011 |

OTHER PUBLICATIONS

PCT International Search Report mailed on Sep. 21, 2011for PCT/IB2011/052330 filed on May 27, 2011 in the name of Gianfranco Passuello.
PCT International Preliminary Report on Patentability mailed on Jul. 23, 2012 for PCT/IB2011/052330 filed on May 27, 2011 in the name of Gianfranco Passuello.
PCT Written Opinion mailed on Sep. 21, 2011 for PCT/IB2011/052330 filed on May 27, 2011 in the name of Gianfranco Passuello.

* cited by examiner

*Primary Examiner* — James Greece
(74) *Attorney, Agent, or Firm* — Steinfl & Bruno, LLP

(57) ABSTRACT

An ophthalmic illumination device has an illuminating body. The illuminating body has a through-opening whose side wall is formed by a member made of an opalescent material. A light source is housed inside the illuminating body and a light-guide adapted to radially convey light beams emitted by the light source towards an axis of the through-opening is positioned between the light source and the opalescent member. The ophthalmic illumination device can generate extremely homogenous shafts of light, while minimizing occurrences of dark portions.

15 Claims, 4 Drawing Sheets

OPHTHALMIC ILLUMINATION DEVICE

CROSS REFERENCE TO RELATED APPLICATIONS

The present application is the US national stage of International Application PCT/IB2011/052330 filed on May 27, 2011, which in turn, claims priority to Italian Patent Application TN2010U000008 filed on May 27, 2010.

The present invention relates to an ophthalmic illumination device and in particular to an illumination device which allows to make evaluations and diagnoses of the tear film of the patient's eye.

The tear film is a liquid structure produced by the lacrimal apparatus of a human being that coats the eyelid conjunctiva and the cornea. Starting from the corneal epithelium, the tear film is made up of three subsequent layers having different functions.

The innermost layer, called mucous layer, is produced by accessory muciparous glands and coats the epithelial cells of eyelid conjunctiva and cornea. The function of the mucus is to make hydrophilic the surface of the cornea, by establishing bonds with the microvilluses of the surface cells of the cornea.

The intermediate layer, called aqueous layer, forms the largest part of the tear film. The aqueous layer is mainly produced by the secretions of the primary and accessory lacrimal glands and is made up of electrolytes and some organic acids, amino acids and proteins having antibacterial and enzymatic functions. The aqueous layer has the main functions of reducing friction deriving from eye and eyelid movements, wiping peeled-off epithelial cells, stemming metabolic waste and removing air impurities.

The outermost layer, called lipid layer, is made up of oils produced by Meibomian glands. The function of the lipid layer is to provide the eyelid edge with a hydrophobic barrier in order to prevent tears from spilling out and to maintain the eye surface wet during sleeping hours, thus also adjusting the evaporation rate of the aqueous layer of the tear itself.

As it is known, quantitative reductions and/or qualitative alterations of the tear film are felt by a patient as eye dryness. The dry-eye syndrome is a generally serious disease because it may generate damages to the outer structures of the eye. In particular, the tear film tends to separate into "fragments", thus exposing the front corneal epithelium and the eyelid conjunctiva to dehydration.

Ageing and improper and excessively long use of contact lenses are among the main causes of eye dryness.

The evaluation of the tear film and the diagnosis of possible diseases such as the dry-eye syndrome are therefore extremely important for the health of a patient and are presently more and more employed by ophthalmologist, as well as by opticians and optometrists specialized in the application of contact lenses.

Several methods and associated instruments allowing to evaluate and diagnose the tear film from both a qualitative and a quantitative point of view are known. The evaluation methods may be either of an invasive or non-invasive type.

Quantitative tests allow to evaluate the amount of basal and/or reflex secretion, whereas qualitative tests allow to evaluate the functionality and the stability of the tear film.

Among qualitative tests, the evaluation of the "Break Up Time" (B.U.T.) of the tear film, which is a stability index of the precorneal tear film, is particularly important. This test, which is of an invasive type, is carried out by instilling fluorescein into the patient's eye and observing the continuity of the tear film through a slit lamp and a specialized cobalt blue filter.

A qualitative test named N.I.B.U.T. (Non Invasive Break Up Time), which allows to evaluate the break up time of the tear film without instilling fluorescein or other substances into the patient's eye, i.e. in a non-invasive way, is known as well.

In order to carry out this type of test it is necessary to project onto the patient's eye a light beam that creates a wide corneal reflection. To this aim, specialized ophthalmic illumination devices are used, e.g. comprising a hemi-spherical bowl in whose concavity a reticule of white lines is drawn on a black background. The image of the reticule, which is projected onto the patient's eye through a shafts of light generated by a light source associated with the hemi-spherical bowl, is reflected by the tear film and can be observed by naked eye or through a slit lamp. The continuity of the tear film is indicated by the regularity of the reticule projected onto the patient's eye, whereas alterations of the reticule indicate the break up of the tear film.

A device of this type is disclosed, for example, in patent GB 2123977 in the name of Smith and Nephew Associated Companies PLC.

Among the ophthalmic devices allowing to carry out the N.I.B.U.T. test, portable instruments are known as well, that can be used in an extremely simple and quick way for preliminary diagnoses without necessarily requiring the use of slit lamps and other equipment that are typically available to an ophthalmologist, an optician or an optometrist.

An example of a portable ophthalmic device is that of the English company Keeler Ltd., known under the trademark TEARSCOPE PLUS. This instrument comprises a handgrip and an illuminating body constrained thereto. The illuminating body comprises a through-opening on whose side wall a reticule of black lines arranged so as to form a grid or concentric circles is obtained by applying a transparent film. Inside the illuminating body a helical-shaped neon lamp is housed coaxially to the through-opening. The side wall of the through-opening is made of an opalescent material, whereby, when the neon lamp is on, the emitted light is able to project the reticule onto the patient's eye, thus allowing an ophthalmologist, an optician or an optometrist to observe it through the through-opening of the device.

This portable device may be combined with a slit lamp, thus making it possible to generate interferences fringes on the tear film allowing to make more accurate diagnoses as well as to evaluate the thickness of the lipid layer.

A portable ophthalmic device similar to the previous one is disclosed in Japanese patent JP 08098811 in the name of Nippon Contact Lens KK. In this case the lamp used as a light source is not helically wound around the through-opening, but it has an annular shape and is arranged within the illuminating body coaxially to the through-opening and at one end thereof.

A problem of the ophthalmic devices described above is that the shafts of light projected by them comprise dark portions caused by the discontinuities of the light sources employed. In the case of the TEARSCOPE PLUS, for instance, the dark portions correspond to the gaps between adjacent coils of the lamp. As a consequence, the patient's eye is not completely illuminated, thus leading to evaluations and diagnoses that are potentially poorly accurate.

Moreover, not all the light emitted by the light sources of the ophthalmic illumination devices is actually projected to the outside of the respective illuminating bodies, this resulting in a poor illumination efficiency and causing waste of electric energy.

Thus there is the need to improve known ophthalmic illumination instruments with particular reference to the continuity and the homogeneousness of the light shaft projected onto the patient's eye, which is an object of the present invention.

An object of the present invention is also to improve the illumination efficiency while reducing the electric energy consumption.

An idea of solution underlying the present invention is to combine the light source housed in the illuminating body with a light-guide suitable to convey the light beams emitted by the light source towards the patient's eye. Thanks to this solution it is possible to generate extremely homogeneous light beams, while minimizing the occurrence of dark portions. The illumination efficiency of the ophthalmic device according to the invention is thus higher than the illumination efficiency of known devices, thereby resulting in a lower electric energy consumption for a same intensity of emitted light.

The light-guide may advantageously be provided with treated surfaces, e.g. silk-finished, sand-blasted or light-etched, which remarkably contribute to make homogeneous and to diffuse the light shaft emitted by the ophthalmic device.

The light source of the ophthalmic device according to the invention may be positioned on a plane inside the illuminating body, allowing to optimize the internal spaces and thus the overall size of the ophthalmic device.

According to a preferred embodiment of the invention, the light source housed inside the illuminating body comprises a plurality of LEDs. The use of LEDs is very advantageous because they are extremely small relative to neon lamps and thus allow to reduce the overall size of the ophthalmic illumination device relative to the size of ophthalmic illumination devices known in the art.

Moreover, LEDs are extremely cheap and long-lasting, allowing to manufacture the ophthalmic device of the invention at a very low cost.

Further, the use of LEDs allows to avoid the flickering problems typical of neon lamps, as well as to ensure a higher chromatic performance and allow a very simple adjustment of the luminous intensity.

Further advantages and features of the ophthalmic device according to the present invention will become clear to those skilled in the art from the following detailed and non-limiting description of an embodiment thereof with reference to the attached drawings, wherein.

Figure 1:
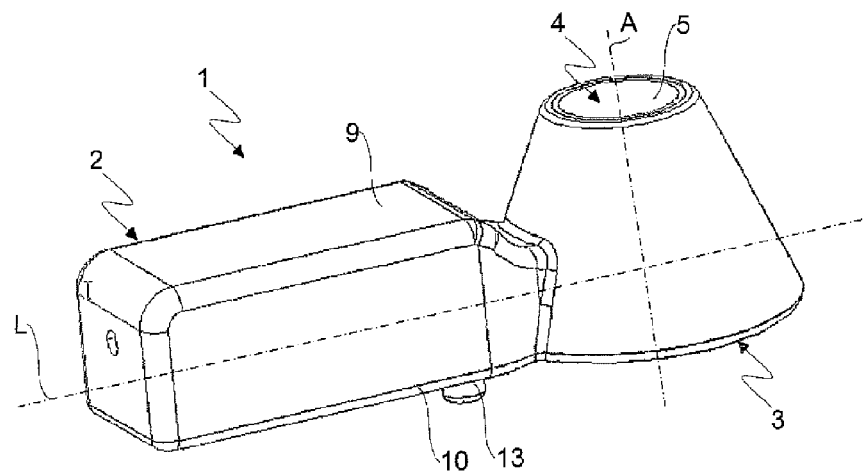
FIGS. 1 and 2 are perspective front and rear views, respectively, showing an ophthalmic device according to the present invention.

Referring to the figures, the ophthalmic illumination device 1 according to the invention comprises a handgrip 2 and an illuminating body 3 connected to the handgrip 2 at one end thereof in a longitudinal direction L and suitable to emit a light shaft towards the eye of a patient. In the shown embodiment, the handgrip 2 has in particular a parallelepiped shape, while the illuminating body 3 has a frusto-conical shape.

It should be understood that the presence of the handgrip 2 is not mandatory for the invention and that the illuminating body 3 might be directly handled by a user or be a part of a fixed diagnostic ophthalmic apparatus, e.g. a slit lamp.

The illuminating body 3 comprises a through-opening 4 whose axis A is perpendicular to the longitudinal direction L defined by the handgrip 2 and whose side wall, e.g. having a cylindrical or frusto-conical shape, is formed of a member 5 made of an opalescent material.

Figure 8:
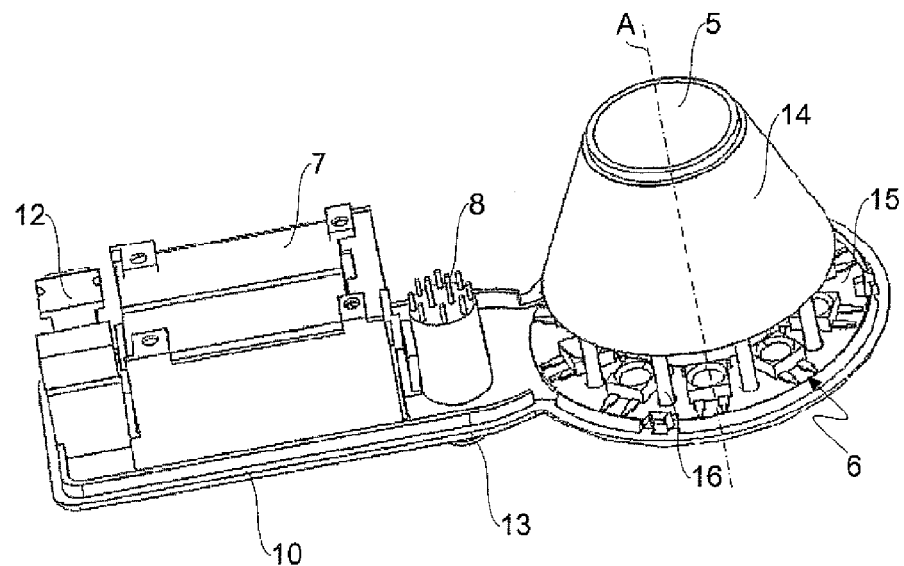
FIG. 8 is a perspective front view showing the ophthalmic device of FIG. 1 without the front half-shell.
Figure 9:
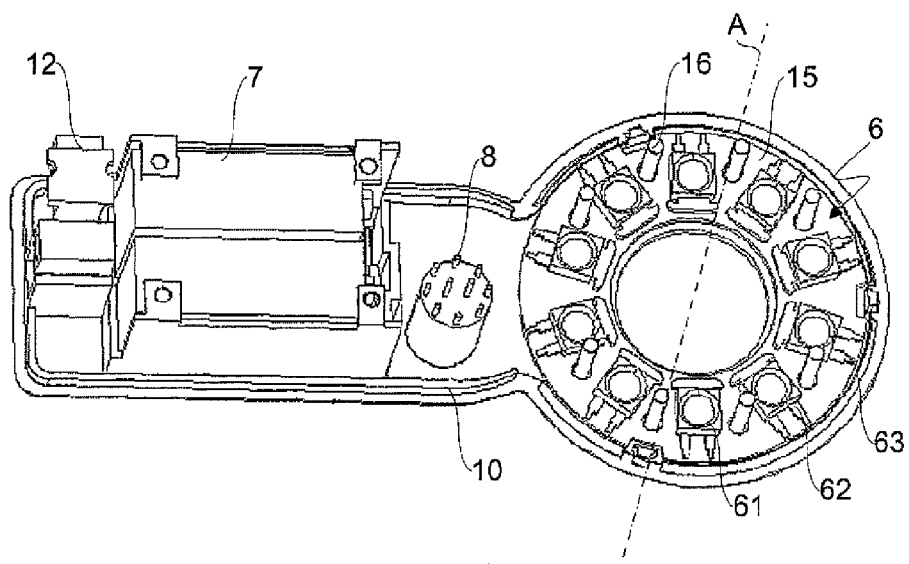
FIG. 9 is a perspective front view similar to that of FIG. 8 and wherein the ophthalmic device is shown without light-guide and opalescent member.

Inside the illuminating body 3, a light source 6 is housed, which is shown in detail in FIGS. 8 and 9, and which projects a light shaft through the opalescent member 5 in an operating condition of the ophthalmic device 1. As it is known, the light shaft projected by the ophthalmic device 1 allows to carry out non-invasive evaluations and diagnoses of the tear film of the patient's eye.

A reticule of lines so arranged as to form a grid or concentric circles (which, as it is known, allows to carry out more accurate evaluations of the tear film, and in particular of its break up time, in a non-invasive way) may be drawn, or obtained by applying a film, on the opalescent member 5.

From a manufacturing point of view, the handgrip 2 and the illuminating body 3 form a single body inside which, in addition to the light source 6, other components are housed, e.g. a compartment 7 for batteries supplying the light source 6 and a electronic control system 8 suitable to allow the adjustment of the luminous intensity of the light source 6.

Due to manufacturing and assembly needs, the single body formed by the handgrip 2 and the illuminating body 3 comprises two half-shells, in particular a front half-shell 9 and a rear half-shell 10. The front half-shell 9 is intended to face the patient's eye during the normal use of the ophthalmic device 1, so that the rear half-shell 10 will face the opposite side, i.e. towards the user.

Due to manufacturing needs again, the opalescent member 5 may be made as a component independent from the half-shells 9 and 10 and in an assembled configuration it is so arranged that the axis A of the through-opening is substantially perpendicular to the two half-shells 9, 10.

Figure 2:
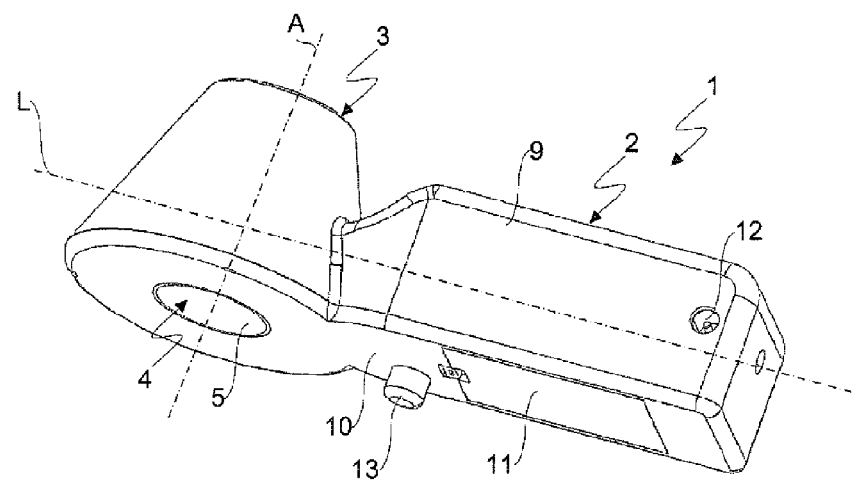
Figure 3:
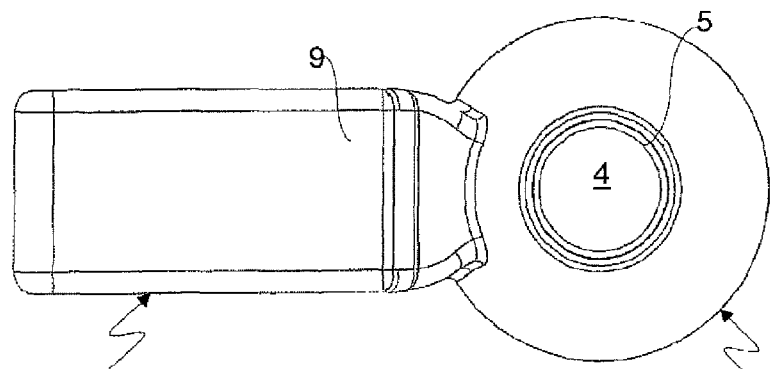
FIGS. 3, 4 and 5 are a top view, a front view and a side view, respectively, of the ophthalmic device of FIGS. 1 and 2.
Figure 4:
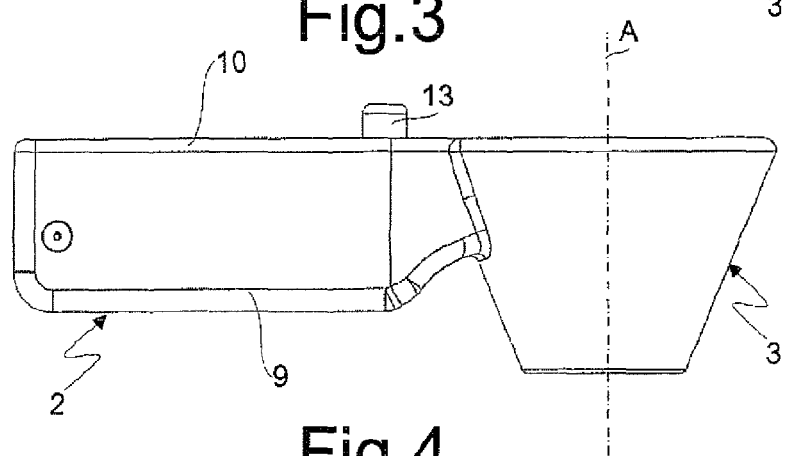
Figure 5:
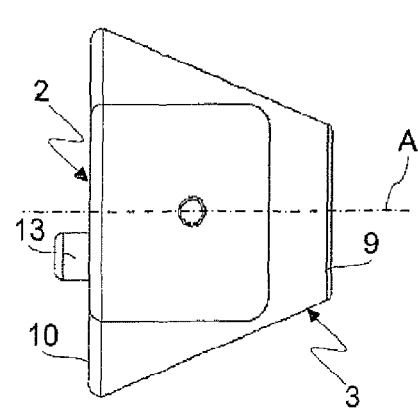
Figure 6:
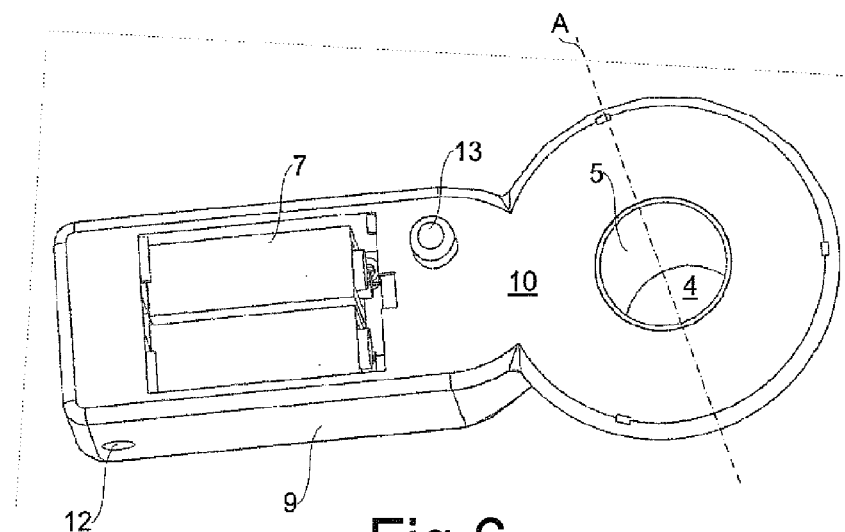
FIG. 6 is a perspective rear view showing the ophthalmic device of FIG. 2 with the battery compartment in an open configuration.
Figure 7:
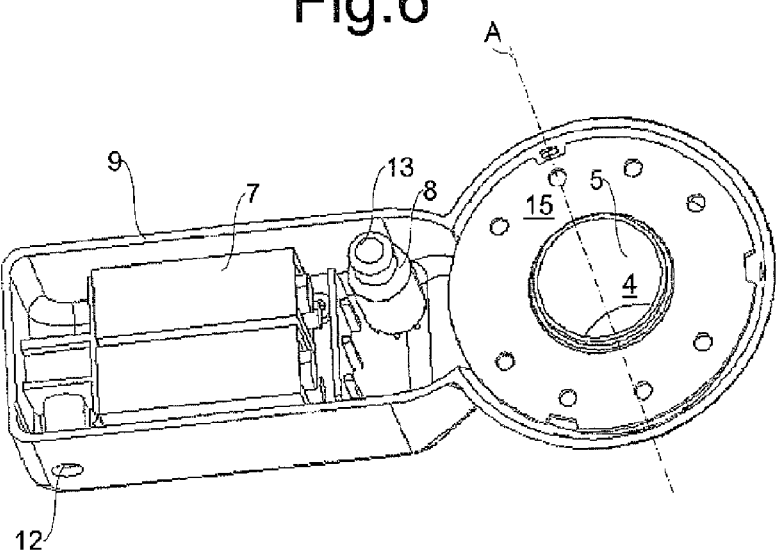
FIG. 7 is a perspective rear view showing the ophthalmic device of FIG. 2 without the rear half-shell.

As shown in FIG. 2, the battery compartment 7 is accessible from the rear half-shell 10 through a removable door 11. The ophthalmic device 1 may also comprise a connector 12 for the connection of a power supply (not shown). In the shown embodiment, the connector 12 faces a side of the front half-shell 9.

In order to allow the adjustment of the luminous intensity of the light source 6, the electronic control system 8 may comprise e.g. a rotatable knob 13 protruding from a circular seat formed in the rear half-shell 10. Alternatively, there may be buttons, sliders and similar adjustment means that are well known to those skilled in the art.

Referring to FIG. 8, the light source 6 is associated with a light-guide 14. In particular, the light-guide 14 is positioned between the light source 6 and the opalescent member 5, thus allowing to radially convey the light beams emitted by the light source 6 towards the axis A of the through-opening 4. In this way it is possible to minimize the number and the size of the dark portions characterizing the light source, thus obtaining a substantially uniform illumination of the opalescent member 5 and thereby a more intense and extremely homogeneous light shaft from the illuminating body 3.

In the shown embodiment the light source 6 is positioned on a plane, e.g. parallel to the base of the rear half-shell 10, and the light-guide 14 has a frusto-conical shape whose larger base faces the light source 6. The light-guide 14 further comprises an axial bore allowing its assembling coaxially to the opalescent member 5.

Advantageously, the light-guide 14 and the opalescent member 5 may form a single body, which allows to optimize the manufacturing and the assembly process of the ophthalmic device 1.

In an operating condition of the ophthalmic device 1, the light beams emitted by the light source 6 hit the larger base of the light-guide 14, pass through it and are deflected by the frusto-conical surface of the light-guide 14, thus being radially conveyed towards the axis A of the through-opening 4 passing through the opalescent member 5 and forming a light shaft.

It should be noted that the light source 6 is positioned at the end of the opalescent member 5 that is opposite to the end intended to face the patient's eye, so that the emitted light beams pass radially through the opalescent member 5 in all its length, thus maximizing the intensity of the light shaft emitted by the illuminating body 3.

The placement of the light source 6 on a plane and the frusto-conical shape of the light guide 14 described above allow to optimize the positioning of the internal components of the ophthalmic device 1 with the aim of reducing its overall size.

However, this configuration of the device is not mandatory for the working of the invention. For example, the light source 6 might be positioned coaxially to the through-opening 4 providing, as in the above-described embodiment, to arrange therebetween a light-guide suitable to radially convey the light beams towards the axis A of the through-opening 4.

With the aim of improving the homogeneousness of the light beams emitted by the light source 6 of the ophthalmic device 1, the light-guide 14 may comprise one or more surface-treated faces, e.g. made by silk finishing, sand-blasting, light-etching and the like.

Preferably, all the faces of the light-guide 14 are surface-treated, thus allowing to maximize the effect of homogenization and diffusion of the light.

In addition or alternatively, it is possible to coat with reflecting films or paints, e.g. silver films or paints, one or more of the sloping surfaces of the light-guide suitable to deflect the light beams emitted by the light source 6, e.g. the frusto-conical surface of the light-guide 14 described above, thus contributing to maximize the effect of homogenization and diffusion of the light shaft emitted by the illuminating body 3.

Referring now in particular to FIGS. 8 and 9, in the shown embodiment the light source 6 comprises a plurality of LEDs 61, 62, 63, . . . positioned on a same plane circumferentially around the through-opening 4 of the ophthalmic device 1. The LEDs 61, 62, 63 are of the cold-light type, in particular white light, which as it is known allows to carry out tests on the tear film while preventing the light shaft from causing its evaporation, thereby altering the evaluation and diagnosis of possible diseases.

The use of LEDs is very advantageous because they are extremely smaller than the neon lamps used in the ophthalmic illumination devices known in the art and thus allow to reduce the overall size of the light source 6 of the ophthalmic device 1 according to the invention.

Advantageously, the LEDs 61, 62, 63 may be mounted on a same printed circuit board 15 positioned parallel to the base of the rear half-shell 10.

As shown in FIG. 9, the printed circuit board 15 may be mounted on one of the half-shells 9, 10 of the ophthalmic device 1, e.g. the rear half-shell 10. To this purpose, the rear half-shell 10 comprises a plurality of posts 16 that, in addition to allow the mounting of the printed circuit board, work also as centering members. As shown in FIG. 8, the posts 16 may also be advantageously used as supporting and/or centering members of the light-guide 14.

The embodiments of the invention herein described and shown are mere examples susceptible of numerous variants. For example, the ophthalmic device 1 might be supplied directly from the mains without the need for batteries, which allows to further reduce the size of the handgrip 2. Moreover, the control system 8 might comprise a user interface of an interactive type, e.g. provided with an LCD display arranged in the handgrip 2, suitable to allow, via a dedicated software, the setting of the illumination parameters of the ophthalmic device 1 and to check its operating condition.

The invention claimed is:

1. A device comprising: an illuminating body having a through-opening,
   a light source housed inside the illuminating body, and
   a light-guide configured to radially convey light beams emitted by the light source towards an axis of the through-opening,
   the illuminating body being configured to emit a light shaft towards an eye of a patient through the through-opening, wherein
      the illuminating body comprises an opalescent member, the opalescent member forming a side wall of the through-opening, the light-guide is positioned between the light source and the opalescent member, thus obtaining a substantially uniform illumination of the opalescent member and a homogeneous light shaft from the illuminating body.

2. The device according to claim 1, wherein the light source is positioned on a plane and the light-guide comprises an axial bore adapted to allow an assembling of the light-guide coaxially to the opalescent member.

3. The device according to claim 2, wherein the light source is positioned on a plane at an end of the opalescent member opposite to an end intended to face the eye of the patient.

4. The device according to claim 2, wherein the light-guide has a frusto-conical shape.

5. The device according to claim 1, wherein the light-guide comprises one or more surface-treated faces, such that improved homogeneity of the light shaft from the illuminating body is obtained.

6. The device according to claim 5, wherein all faces of the light-guide are surface-treated.

7. The device according to claim 1, wherein the light-guide comprises sloping surfaces adapted to deflect light beams emitted by the light source and wherein the sloping surfaces are coated with reflecting films or paints.

8. The device according to claim 1, wherein the light source comprises a plurality of LEDs.

9. The device according to claim 8, wherein the plurality of LEDs are positioned on a same plane circumferentially around the through-opening.

10. The device according to claim 9, wherein the plurality of LEDs are mounted on a same printed circuit board.

11. The device according to 1, further comprising a handgrip and wherein the handgrip and the illuminating body form a single body comprising a front half-shell and a rear half-shell.

12. The device according to claim 10, comprising a handgrip, wherein said handgrip and the illuminating body form a single body comprising a front half-shell and a rear half-shell, the same printed circuit board being constrained to the rear half-shell through a plurality of posts, the posts being also centering members of the same printed circuit board and supporting and/or centering members of the light-guide.

13. The device according to claim 1, wherein the light-guide and the opalescent member form a single body.

14. An apparatus comprising the device according to claim 1.

15. The device of claim 1 wherein the light guide is a surface treated light guide.

* * * * *